United States Patent  
Vogt (10) Patent No.: US 10,307,195 B2
(45) Date of Patent: Jun. 4, 2019

(54) DEVICE AND METHOD FOR STORING AND MIXING A BONE CEMENT

(71) Applicant: Heraeus Medical GmbH, Wehrheim (DE)

(72) Inventor: Sebastian Vogt, Erfurt (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 254 days.

(21) Appl. No.: 15/281,224

(22) Filed: Sep. 30, 2016

(65) Prior Publication Data

US 2017/0095283 A1   Apr. 6, 2017

(30) Foreign Application Priority Data

Oct. 2, 2015  (DE) .................. 10 2015 116 797

(51) Int. Cl.
  *B01F 7/16* (2006.01)
  *A61B 17/88* (2006.01)
  (Continued)

(52) U.S. Cl.
  CPC ...... *A61B 17/8833* (2013.01); *A61B 17/8827* (2013.01); *B01F 3/1221* (2013.01);
  (Continued)

(58) Field of Classification Search
  CPC ..................................................... B01F 7/161
  (Continued)

(56) References Cited

U.S. PATENT DOCUMENTS 2,825,134 A   3/1958  Hicks
3,475,010 A  10/1969  Cook et al.
(Continued)

FOREIGN PATENT DOCUMENTS

CN   1972648 A    5/2007
CN   103801216 A  5/2014
(Continued)

OTHER PUBLICATIONS

English translation of Japanese Office Action corresponding to Japanese application No. 2016-185097 dated Jun. 10, 2018.
(Continued)

*Primary Examiner* — David L Sorkin
(74) *Attorney, Agent, or Firm* — Norris McLaughlin, P.A.

(57) ABSTRACT

Devices and methods mix a bone cement and comprise at least one cartridge, wherein the cartridge comprises in its interior a cylindrical mixing chamber, a discharge piston movable in the cylindrical mixing chamber in the longitudinal direction and sealable against the walls of the mixing chamber, a mixing device for thoroughly mixing the content of the mixing chamber, which is arranged in the interior of the mixing chamber. The mixing device is operable externally via a mixing rod and the mixing rod is guided through a passage in the discharge piston such that it can be rotated and displaced in the longitudinal direction by the discharge piston. The cartridge comprises a discharge opening opposite the discharge piston, wherein, in the mixing chamber, a first component is contained between the discharge piston and the discharge opening, wherein a monomer fluid as a second component is introducable through the discharge opening into the mixing chamber. The device further comprises a locking element with which the mixing rod is affixable to the discharge piston such that the discharge piston is movable by means of the mixing rod in the mixing chamber in the longitudinal direction.

23 Claims, 5 Drawing Sheets (51) Int. Cl.
*B01F 13/00* (2006.01)
*B01F 3/12* (2006.01)
*B01F 15/00* (2006.01)
*B01F 15/02* (2006.01)
*B01F 11/00* (2006.01)
*A61B 90/00* (2016.01)

(52) U.S. Cl.
CPC .......... *B01F 7/161* (2013.01); *B01F 11/0054* (2013.01); *B01F 13/0023* (2013.01); *B01F 15/00025* (2013.01); *B01F 15/00506* (2013.01); *B01F 15/0206* (2013.01); *B01F 15/0258* (2013.01); *B01F 15/0279* (2013.01); *A61B 17/8825* (2013.01); *A61B 2017/8838* (2013.01); *A61B 2090/037* (2016.02); *B01F 2215/0029* (2013.01)

(58) Field of Classification Search
USPC ........................................ 366/139, 189, 195
See application file for complete search history.

(56) References Cited

U.S. PATENT DOCUMENTS

| | | | |
|---|---|---|---|
| 4,671,263 A | 6/1987 | Draenert | |
| 4,758,096 A | 7/1988 | Gunnarsson | |
| 4,966,468 A * | 10/1990 | Bruning | B65D 81/3255 222/190 |
| 4,973,168 A | 11/1990 | Chan | |
| 5,100,241 A | 3/1992 | Chan | |
| 5,252,301 A | 10/1993 | Nilson et al. | |
| 5,273,190 A * | 12/1993 | Lund | B05C 17/00553 222/105 |
| 5,344,232 A | 9/1994 | Nelson et al. | |
| 5,551,778 A | 9/1996 | Hauke et al. | |
| 5,586,821 A | 12/1996 | Bonitati et al. | |
| 5,588,745 A | 12/1996 | Tanaka et al. | |
| 5,624,184 A | 4/1997 | Chan | |
| 5,997,544 A | 12/1999 | Nies et al. | |
| 6,033,105 A | 3/2000 | Barker et al. | |
| 6,709,149 B1 | 3/2004 | Tepic | |
| 7,513,679 B2 * | 4/2009 | Grebius | A61B 17/8825 366/189 |
| 7,736,049 B2 | 6/2010 | Keller | |
| 7,938,572 B2 | 5/2011 | Lidgren et al. | |
| 8,167,835 B2 | 5/2012 | Keller | |
| 8,297,831 B2 | 10/2012 | Lidgren et al. | |
| 8,662,736 B2 | 3/2014 | Vogt et al. | |
| 8,662,737 B2 | 3/2014 | Lidgren et al. | |
| 9,676,120 B2 | 6/2017 | De Vries et al. | |
| 9,694,514 B2 | 7/2017 | Vogt | |
| 2007/0217282 A1 | 9/2007 | Lidgren et al. | |
| 2010/0008181 A1 | 1/2010 | Lidgren et al. | |
| 2010/0329074 A1 | 12/2010 | Vogt et al. | |
| 2011/0270260 A1 | 11/2011 | Grebius | |
| 2011/0273954 A1 | 11/2011 | Greter et al. | |
| 2012/0026825 A1 | 2/2012 | Vogt et al. | |
| 2012/0132675 A1 | 5/2012 | Vogt et al. | |
| 2013/0064033 A1 | 3/2013 | Lidgren et al. | |
| 2013/0098942 A1 | 4/2013 | Greter | |
| 2013/0135957 A1 | 5/2013 | Vogt et al. | |
| 2013/0223181 A1 | 8/2013 | De Vries et al. | |
| 2014/0098629 A1 | 4/2014 | Greter | |
| 2014/0126320 A1 | 5/2014 | Vogt | |
| 2014/0198601 A1 | 7/2014 | Lidgren et al. | |
| 2015/0367301 A1 | 12/2015 | Vogt | |

FOREIGN PATENT DOCUMENTS

| | | |
|---|---|---|
| DE | 1 805 110 A1 | 11/1969 |
| DE | 3 640 279 A1 | 6/1987 |
| DE | 69812726 T2 | 2/2004 |
| DE | 10 2009 031 178 B3 | 9/2010 |
| DE | 10 2010 004342 A1 | 7/2011 |
| DE | 102010052323 A1 | 5/2012 |
| DE | 10 2012 024710 A1 | 5/2014 |
| DE | 10 2014 108569 B3 | 10/2015 |
| EP | 0 692 229 A1 | 1/1996 |
| EP | 1 005 901 A2 | 6/2000 |
| EP | 1 016 452 A2 | 7/2000 |
| EP | 1 020 167 A2 | 7/2000 |
| EP | 2 108 324 A1 | 10/2009 |
| JP | H4-507200 | 12/1992 |
| JP | 2008 503317 A | 2/2008 |
| JP | 2013-136050 | 7/2013 |
| JP | 2014 121520 A | 7/2014 |
| WO | 94/26403 A1 | 11/1994 |
| WO | 99/67015 A1 | 12/1999 |
| WO | 2010/083616 A1 | 10/2009 |
| WO | 2011083095 A1 | 7/2011 |

OTHER PUBLICATIONS

Search report from corresponding Taiwan Application No. 105131560 dated May 24, 2017.
Notice of Reasons for Rejection issued in corresponding Japanese Application dated Aug. 29, 2017.

* cited by examiner

DEVICE AND METHOD FOR STORING AND MIXING A BONE CEMENT

This application claims foreign priority benefit under 35 U.S.C. 119 of German Application No. DE 10 2015 116 797.2 filed Oct. 2, 2015.

The invention relates to a device for mixing a bone cement. The invention additionally relates to a method for mixing a bone cement. Further, the invention relates to a device and a method for storing the initial components of a bone cement and for mixing the initial components.

The subject of the invention is thus also a device for storing and mixing polymethyl methacrylate bone cement and a method for mixing polymethyl methacrylate bone cement.

Polymethyl methacrylate bone cements (PMMA bone cements) can be traced back to the foundation work of Sir Charnley. PMMA bone cements consist of a liquid monomer component and a powder component. The monomer component generally contains the monomer methyl methacrylate and an activator (N, N-dimethyl-p-toluidine) dissolved in it. The powder component, also known as bone cement powder, comprises one or more polymers, an X-ray opaquer and the initiator dibenzoyl peroxide. The polymers of the powder component are produced on the basis of methyl methacrylate and comonomers such as styrene, methyl acrylate or similar monomers using polymerisation, preferably suspension polymerisation. When the powder component is mixed with the monomer component, a plastically deformable dough, the actual bone cement, is created as a result of the swelling of the polymers of the powder component in the methyl methacrylate. While the powder component is mixed with the monomer component, the activator N, N-dimethyl-p-toluidine reacts with dibenzoyl peroxide while forming radicals. The radicals formed initiate the radical polymerisation of the methyl methacrylate. With continuing polymerisation of the methyl methacrylate, the viscosity of the cement paste increases until it rigidifies.

The monomer most frequently used in polymethyl methacrylate bone cements is methyl methacrylate. Redox initiator systems generally consist of peroxides, accelerators and in some cases suitable reduction agents. Radicals are only formed when all constituents of the redox initiator systems interact. For this reason, the constituents of the redox initiator system are arranged in separate initial components in such a manner that they cannot trigger any radical polymerisation. With a suitable composition, the initial components are sufficiently stable for storage purposes. Only when the two initial components are mixed to form a cement paste do the constituents of the redox initiator system, which were previously separately stored in the two pastes, liquids or powders, react, wherein radicals are formed which trigger the radical polymerisation of the at least one monomer. Using the monomer, the radical polymerisation then leads to the formation of polymers, wherein the cement paste fully hardens.

PMMA bone cements can be mixed in suitable mixing vessels with the aid of spatulas by mixing the cement powder with the monomer liquid. Here, inclusions of air bubbles may occur in the bone cement paste which can negatively impact the mechanical properties of the hardened bone cement.

For this reason, mixing bone cement powder with the monomer fluid in vacuum mixing systems is preferred, since through mixing in the vacuum, air inclusions are for the most part removed from the cement paste. A plurality of vacuum cementing systems are disclosed, including for example: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, U.S. Pat. No. 5,344,232 A. With the vacuum cementing systems presented, it is necessary to connect an external vacuum pump in order to generate the underpressure. These are generally operated with compressed air using the Venturi principle. It is additionally possible to use electrically driven vacuum pumps in order to generate the vacuum.

A further development in cementing technology comes in the form of cementing systems, in which both the cement powder and the monomer fluid are already packed in separate compartments of the mixing systems and are not mixed together until directly prior to the cement application in the cementing system. Such full-prepacked systems have been recommended in EP 0 692 229 A1, DE 10 2009 031 178 B3, U.S. Pat. Nos. 5,997,544 A, 6,709,149 B1, DE 698 12 726 T2 and U.S. Pat. No. 5,588,745 A. These mixing systems also require an external vacuum source. The patent DE 10 2009 031 178 B3 here discloses a vacuum mixing device with a two-part discharge piston. Here, a two-part piston system for closing a full-prepack cement cartridge is recommended, in which a combination of a gas permeable sterilisation piston and a gas impermeable sealing piston is used.

When vacuum mixing systems are used for cementing purposes, external vacuum pumps must be provided. These vacuum pumps are costly and must be cleaned following application. Further, vacuum hoses for connecting the vacuum pumps with the vacuum mixing systems are also required. These vacuum hoses must be supplied with the vacuum mixing systems. Before mixing with a vacuum mixing system, therefore, the vacuum pump must first be set up in the operating theatre (op theatre) and an energy source such as compressed air or an electric current must be connected. Then the vacuum pump is connected to a vacuum hose with the vacuum mixing system. This assembly step costs valuable op time and is subject to potential error. The vacuum pump and the connection lines to the vacuum mixing system and to external energy sources and supply lines require space and can potentially cause stumbling or present obstacles which can impede the occasionally hectic process during an operation.

WO 2011/083 095 A1 discloses a mixing device for bone cement in which a piston can be moved over a threaded rod in a cement cartridge in order to generate an underpressure in the mixing chamber of the cartridge. A mixing paddle is arranged on a rod as a mixing device and in the rod, a monomer fluid is located as a component of the bone cement. The disadvantage of this is that an additional passage is required through which alongside the mixing paddle, an additional movable part of the device, namely the piston, must be guided in a sealed manner. The gas-tight and pressure-tight seal is particularly complex with passages with a supported thread. Additionally, both sides of the cartridge are blocked by the respective passages. Sterilisation of the interior chamber is also no longer possible shortly prior to using the device. The system is also unsuitable for longer storage of a monomer fluid, since neither the plastic of the rod nor the film which can be punctured, which is glued on to cover the interior chamber of the rod on the end pointing inwards, can hold the strongly diffusion-capable and chemically aggressive monomer fluid for a long period of time. If contact occurs too early between the bone cement powder and the monomer fluid, the mixture hardens and can then no longer be opened by the pin on the piston designed for the purpose.

The object of the invention is to overcome the disadvantages of the prior art. In particular, a device is to be provided for mixing bone cement which enables simple operation and in which two initial components of the bone cement can be securely mixed without needing to revert to additional energy storage devices or supply lines for this. Additionally, an easy to operate device is to be provided for storing and mixing PMMA bone cement in which the initial components of the bone cement can be stored for as long as possible, and at the same time can be securely combined and mixed. A further object is to provide a method for producing bone cement, which is preferably also suited to storing the initial components. The device to be developed should as far as possible be a full-prepacked cementing device for powder fluid polymethyl methacrylate bone cements. The device should be inexpensive to produce and enable error-free application. Additionally, it should be possible to implement the device and the method without an energy storage device and without connections for power, compressed air or other energy sources. Preferably, it should be possible to operate the device manually and in as simple a manner as possible. For medical applications, the device should be designed as a disposable product, so that as far as possible, no metals or hazardous substances should be used and a structure made of plastic as far as possible is aimed for.

Further, the disadvantages of the known vacuum mixing systems with an external vacuum source are to be overcome without having to maintain an underpressure over a long period of time. The device should be kept simple to the maximum degree and permit an underpressure to be generated at least once in a cement cartridge in relation to the ambient atmosphere. Further, it can be advantageous when the vacuum mixing system is capable of enabling a transfer of monomer fluid from a monomer vessel into a cartridge filled with cement powder or cement paste.

Further, the object of the invention is to develop a simple, closed device in which the polymer methyl methacrylate bone cement powder and monomer fluid are stored in separate compartments and can then be mixed. It should be possible for the medical user to combine and mix the polymethyl methacrylate bone cement powder with the monomer fluid within the device without both cement components coming into contact with the medical user. No contact between the medical user and the polymethyl methacrylate bone cement powder and the monomer fluid should be possible under any circumstances. The device should be designed in such a manner that a transfer of the monomer fluid into the bone cement powder is conducted via a vacuum or underpressure, without the use of external vacuum pumps. Here, it is important that the device functions correctly and reliably without external energy sources such as compressed air, vacuum or electrical current, including under the simplest external conditions. It should be possible to use the device autonomously, without additional technical equipment. Further, the number of components of the device should be as low as possible. As far as possible, a separate pump integrated in the device should be avoided.

The main component of the polymethyl methacrylate bone cement as a mixing product should be a powder and the two components should be present in the form of a fluid.

The objects of the invention are attained by a device for mixing a bone cement, the device comprising at least one cartridge, wherein the cartridge comprises a cylindrical mixing chamber in its interior, a discharge piston which is movable in the longitudinal direction in the cylindrical mixing chamber and which is sealed against the walls of the mixing chamber, a mixing device for thoroughly mixing the content of the mixing chamber arranged in the interior of the mixing chamber, wherein the mixing device is operated externally via a mixing rod and wherein the mixing rod can be rotated via a passage in the discharge piston and is guided through the discharge piston in such a manner that it can be displaced, wherein the cartridge comprises a discharge opening opposite the discharge piston, wherein in the mixing chamber, a first component of the bone cement is contained between the discharge piston and the discharge opening, wherein a monomer fluid is introducable as a second component of the bone cement through the discharge opening into the mixing chamber, and wherein the device comprises an affixing element with which the mixing rod is affixable or is affixed to the discharge piston in such a manner that the discharge piston can be moved by means of the mixing rod in the longitudinal direction in the mixing chamber.

The up and down directions relate to the cartridge and the entire device, wherein the discharge opening of the cartridge is arranged on the lower end of the cartridge and the discharge piston is inserted into the upper end of the cartridge. The cylinder axis of the mixing chamber thus extends from top to bottom and the discharge piston is driven forward from top to bottom in order to extrude the contents of the cartridge (the readily mixed bone cement) through the discharge opening.

The discharge opening is thus named since through it, the mixed bone cement is to be forced out of the mixing chamber wherein the discharge piston is driven in the direction of the discharge opening, even though the discharge opening is also used to introduce the monomer fluid.

Preferably, the discharge piston is cylindrical and is suitably formed for closing the cylindrical mixing chamber.

The first component of the bone cement is preferably a bone cement powder, particularly preferred a PMMA bone cement powder. The second component of the bone cement is the monomer fluid. The bone cement paste is produced by mixing the bone cement powder with the monomer fluid within the mixing chamber with the mixing device.

The discharge opening can be formed as a nozzle on the side pointing to the interior of the mixing chamber, preferably as a nozzle as described in U.S. Pat. No. 8,662,736 B2.

With devices according to the invention it can be provided that the mixing rod is detachably affixable or is detachably affixed to the discharge piston.

As a result, the mixing device which is connected to the mixing rod can also be moved with the mixing rod following the movement of the discharge piston, wherein the fixed attachment of the mixing rod to the discharge piston is detached.

With a further development of the present invention, it is recommended that in the discharge opening or in front of the discharge opening, a filter is provided which is impermeable for powder but permeable for fluids, which closes or covers the discharge opening.

Here, the first component of the bone cement is in powder form. As a result, it is prevented that the first component of the bone cement can penetrate the filter into the feed line to the monomer fluid, react prematurely with the monomer fluid there and harden, and then block the feed line into the mixing chamber. Thus it is also prevented that the device is unintentionally no longer ready for operation.

According to a preferred embodiment, with devices according to the invention it can be provided that at least one latching element is provided on the discharge piston, which grips into at least one counter-latching means on the cartridge in such a manner, or is suitable for gripping into at least one counter-latching means in such a manner, that the discharge piston can no longer be moved in the direction away from the discharge opening beyond the at least one latching position, wherein preferably the at least one latching element is arranged on a side sheath surface of the discharge piston and the at least one counter-latching means is arranged on the inner wall of the mixing chamber.

In a particularly preferred embodiment, the at least one latching element can latch detachably with the at least one counter-latching means. The detachment of the at least one latching element from the at least one counter-latching means can be conducted manually, in particular with the aid of an operating element or through the axial force impact on the discharge piston in the direction of the discharge opening. After the at least one latching element is detached from the at least one counter-latching means, the discharge piston should be movable in the direction of the discharge opening in the mixing chamber. In a very particularly preferred embodiment, a movement of the discharge piston in the direction away from the discharge should then also be precluded.

Due to the at least one latching element and the at least one counter-latching means, it is achieved that the discharge piston can no longer be pressed out of the cartridge so far that a gas permeable connection can be created from the environment into the mixing chamber of the cartridge, as is recommended in the further text (see further below), and if necessary with a further latching position can also not be unintentionally pressed upwards out of the cartridge.

With devices with at least one latching element, it can be provided that at least one of the at least one latching elements can be operated externally via at least one operating element, wherein preferably, the operating element is connected to that at least one of the at least one latching elements and protrudes over the upper edge of the cartridge, wherein the upper edge of the cartridge lies opposite the discharge opening, wherein preferably, the operating element is connected as a single piece with the at least one of the at least one latching elements.

The operating element and the latching element are preferably structured in the same way as the arresting device of a cartridge in accordance with DE 10 2010 052 323 A1. The disclosure content of DE 10 2010 052 323 A1 is thus adopted through reference.

Due to these measures, operation is simplified, since the latching elements and thus the latching mechanism are detachable and easy to manually operate externally.

According to a particularly preferred further development of the present invention, it can be provided that the discharge piston comprises a gas impermeable upper side which faces away from the discharge opening and a gas permeable underside, which is impermeable for powder particles, which faces towards the discharge opening, wherein the gas permeable underside is connected via at least one passage in the discharge piston with at least one side opening in the side surface of the discharge piston, so that the mixing chamber is gas-permeably connected with the environment of the cartridge when the at least one opening in the side surface of the discharge piston is not covered by the inner wall of the mixing chamber of the cartridge.

Here it can be provided that the gas permeable underside of the discharge piston is structured with the aid of a gas permeable pore disc, wherein the pore disc is a part of the discharge piston. The pore disc is preferably impermeable for cement powder and permeable for gas.

Through these measures, the discharge piston, if it is only inserted so far into the cartridge that the at least one opening in the side surface of the discharge piston is not covered by the inner wall of the mixing chamber of the cartridge, can be used for gassing the mixing chamber with a sterilising gas. Additional components or a complex conversion of the device can thus be avoided. In the sterilisation position, the discharge piston also prevents bone cement from reaching the outside.

The advantage of such a device is that the interior of the device and also the cement powder can be sterilised by means of gaseous ethylene oxide, wherein the gas exchange occurs via a pore disc which prevents bone cement powder from exiting. Through deeper insertion of the discharge piston into the cartridge, the latter can then be evacuated without the gas permeable discharge piston required for the gas exchange during sterilisation having to be removed when opening the cartridge.

Further, it is here recommended that the discharge piston comprises an upper circumferential seal between the gas impermeable upper side of the discharge piston and the at least one side opening and a lower circumferential seal between the gas permeable underside and the at least one side opening, which seal the discharge piston against the inner wall of the mixing chamber, or are suitable for sealing the discharge piston against the inner wall of the mixing chamber, when the discharge piston has been inserted sufficiently deeply into the cartridge in the direction of the discharge opening.

The seals preferably lie on the inner wall of the mixing chamber in a gas-tight manner.

Thus it is achieved that the mixing chamber is closed with the exception of the at least one passage when the discharge piston is inserted into the cartridge in the sterilisation position. When the discharge piston is in the sterilisation position, only the lower circumferential seal is inserted into the cartridge, and the upper circumferential seal lies exposed, so that the inner chamber of the cartridge, i.e. the mixing chamber, is opened outwards through the at least one passage. When the discharge piston is inserted further into the cartridge in the direction of the discharge opening, from a certain position, the upper circumferential seal also lies with its full circumference on the inner wall of the cartridge, so that then, the inner chamber of the cartridge is closed outwards in an airtight manner by the discharge piston. As a result, the discharge piston is then in the pump position and can be used as a manually operated pump for suctioning in the monomer fluid.

Through the measures described, therefore, the discharge piston can be simultaneously used for powder-tight sterilisation, for pumping the fluid, and later for expelling the bone cement paste from the cartridge. This multiple use entails a simplification of the structure and thus as a result a lower susceptibility to errors and error functions of the device, as well as lower production costs.

It can also be provided that at least two latching positions are provided for the discharge piston, wherein the at least one side opening lies exposed in a first latching position and in a second latching position, the at least one side opening is covered, wherein preferably, in the first latching position the discharge piston is only sealed against the mixing chamber by the lower circumferential seal, and in the second latching position, the discharge piston is sealed against the mixing chamber by the upper and lower seal.

As a result, it is achieved that in the sterilisation position, the discharge piston does not slip unintentionally out of the cartridge, and in the pump position, the at least one passage is not unintentionally opened outwards. Thus the application and operation of the device is simplified.

Preferred embodiments can also be characterized by the fact that on the mixing rod, a manually operated actuation element is attached, preferably a handle element which can be operated single-handedly is attached.

Thus, the mixing and pump processes can be easily manually conducted.

Further it can be provided that the affixing element is a screw cap which encloses the mixing rod and which can be screwed onto or into a counter-thread on the discharge piston in such a manner that the screw cap or the passage through the discharge piston presses onto the mixing rod in such a manner that the mixing rod is affixed against the discharge piston, or the affixing element is at least one pin which is to be inserted through at least one passage in the mixing rod, or which is to be inserted into at least one recess in the mixing rod, so that the mixing rod should or can no longer be inserted into the mixing chamber, wherein preferably, the at least one passage or the at least one recess is positioned in such a manner that the mixing device lies on the underside of the discharge piston facing towards the discharge opening when the mixing rod is affixed against the discharge piston with the at least one pin.

With the variant with the screw cap, it can be provided that the thread of the screw cap or the counter thread is slit on the discharge piston in the longitudinal direction.

These locking elements are easy to operate and are sufficiently stable in order to guarantee an affixation of the mixing rod against the discharge piston for a pump process.

It can additionally be provided that the free volume in the mixing chamber which is not taken up by the first component and the discharge piston when the discharge piston is arranged in the cartridge at a maximum distance in the direction away from the discharge opening is at least as large as the volume of the monomer fluid to be introduced and all connection lines provided between the monomer fluid and the mixing chamber.

This ensures that the capacity of the discharge piston, when it is used for pumping, is sufficiently large in order to pump monomer fluid in a sufficient quantity through the connection lines into the mixing chamber.

It can also be provided that the mixing rod comprises a predetermined breaking point which is arranged directly above the upper side of the discharge piston or locking element when the mixing rod is pulled out of the mixing chamber in such a manner that the mixing device lies on the underside of the discharge piston.

The upper side of the discharge piston is here the side of the discharge piston which faces away from the discharge opening. Accordingly, the underside of the discharge piston is the side of the discharge piston which faces towards the discharge opening.

As a result, the mixing rod and if necessary the handle can be broken off and removed before the cartridge is inserted with the discharge piston into an extrusion device. The mixing rod would be a hindrance in the extrusion device.

The objects which form the basis of the present invention are also attained by means of such a device for storing initial components of the bone cement and for mixing the bone cement, in particular a full-prepacked cementing device with which a connection line is provided which is connected to the discharge opening and which connects the mixing chamber in a fluid permeable manner with a vessel, wherein in the vessel, a monomer vessel with a monomer fluid contained therein can be inserted or is contained, wherein the monomer vessel should or can be opened in the device and the monomer fluid should be suctioned into the mixing chamber through the connection line, wherein an underpressure is generated in the mixing chamber by a movement of the discharge piston away from the discharge opening.

As a result, it is achieved that the device is also well suited for the long-term storage of the initial components of the bone cement, and that the user cannot easily come into contact with the initial components of the bone cement.

With devices according to the invention which are also suitable for storing the initial components, it can be provided that in the vessel, at least one passage is provided, wherein the at least one passage connects the vessel to the environment in a gas permeable manner.

The container comprises the at least one passage so that through the at least one passage, gases can escape when gas is pressed out of the mixing chamber, and air can then flow in when the monomer fluid is suctioned into the mixing chamber. This ensures that on the one hand, a good vacuum or a good underpressure can be generated in the mixing chamber and that the monomer fluid can easily be suctioned out of the vessel for the monomer fluid into the mixing chamber without an underpressure or a vacuum arising between the monomer fluid and the vessel for the monomer fluid, which counteracts the flow of the monomer fluid in the mixing chamber.

Further, it can be provided that the connection line between the vessel and the mixing chamber of the cartridge comprises a loop which points upwards, wherein the highest point of the loop lies above an opening below the monomer vessel which is arranged in the vessel.

When the device is correctly set up, it can thus be ensured that the monomer fluid cannot flow unintentionally into the cartridge without the effect of the underpressure generated with the discharge piston, and there unintentionally react prematurely with the bone cement powder and harden. The loop thus acts as a siphon. As a result, a situation can be prevented whereby the monomer fluid reaches the inner chamber of the cartridge via the fluid line when the monomer vessel (the monomer glass ampule) in the vessel is opened. Due to this inverted U-shaped loop of the connection line, it is achieved that prior to a movement of the discharge piston as a pump piston, the monomer fluid remains in the vessel until the peak in the fluid line or connection line is reached, as a result of which a premature entry of the monomer fluid into the cement powder is prevented. In particular with highly viscous cements, a premature contact of already low volumes of monomer fluid with the cement powder can lead to adhesion of the connection line or of a line means designed in the form of a nozzle, as described in U.S. Pat. No. 8,662,736 B2. The connection line can be transparent or translucent, so that the user can visually monitor the monomer transfer. For this purpose, a viewing window can preferably be provided in the device or in a housing of the device, through which the loop can be seen with the highest peak.

The monomer vessel is preferably a glass ampule which can be broken open, which contains the monomer fluid, or a multiple-layer compound film bag which contains the monomer fluid, wherein preferably, the multiple-layer compound film bag is a multiple-layer compound film bag coated with aluminium. Preferably, the glass ampules have a cylindrical ampule body.

Glass ampules and multiple-layer compound film bags are capable of retaining the monomer fluid for a long period of time without the monomer fluid being able to escape. As a result, the device can also be used for storing the initial components over a long period of time.

With such devices, it can be provided that the device comprises an opening facility with which the monomer vessel in the vessel should be opened, preferably without opening the device during the process or without opening the vessel.

This prevents the user from coming into contact with the monomer fluid when opening the monomer vessel.

Further, it can be provided that the device comprises a foot part which is connected to the cartridge and on which the vessel is also attached, wherein preferably, the cartridge is detachably connected to the foot part, and in a particularly preferred manner is detachably connected to the foot part via a thread.

As a result, the device can easily be set up on a table and is therefore convenient to operate. Erroneous operation due to incorrect setting up can therefore also be precluded. Additionally, the foot part can be used for connecting and stabilising all elements of the device.

The objects which form the basis of the invention are further attained by means of a method for producing a bone cement from a first component and a monomer fluid as a second component, in particular with a device according to the invention, in which
 a mixing rod is affixed, or is already affixed, with the aid of a locking element with a discharge piston,
 the discharge piston is moved away from a discharge opening and as a result, an underpressure forms in the mixing chamber, wherein preferably, the discharge piston is moved manually with the aid of the mixing rod,
 with the underpressure, a monomer fluid is suctioned into the mixing chamber,
 the mixing rod is detached from the discharge piston and the first component of the bone cement and the monomer fluid are mixed in the mixing chamber with a mixing device through manual movement of the mixing rod to form a bone cement paste.

Additionally, it can be provided that after affixing the mixing rod, the discharge piston is inserted sufficiently deeply into the mixing chamber that gas is pressed out of the mixing chamber through the discharge opening before the discharge piston is moved away from the discharge opening.

With methods according to the invention, it can be provided that the mixing chamber is initially connected to the environment of the cartridge via the discharge piston, wherein the device including the mixing chamber is sterilised through evacuation and introduction of a sterilising gas, in particular ethylene oxide,
 subsequently, the discharge piston is moved in the direction of the discharge opening, so that the gas permeable openings in the discharge piston are covered by the inner wall of the mixing chamber, and
 subsequently, the discharge piston is inserted sufficiently deeply into the mixing chamber that gas is pressed out of the mixing chamber through the discharge opening, before the discharge piston is moved away from the discharge opening,
 wherein preferably, the monomer vessel in the vessel of the device is then opened before the discharge piston is moved away from the discharge opening.

The cartridge comprises the mixing chamber or respectively the mixing chamber is arranged inside the cartridge.

When the mixing chamber of the cartridge is evacuated, the discharge piston is preferably secured or bound against the cartridge with the aid of the at least one latching element and the at least one counter-latching means. The monomer vessel can also be opened directly before moving the discharge piston in the direction of the discharge opening. Then the gas is pressed out of the mixing chamber of the cartridge through the connection line and through the monomer fluid in the vessel. The vessel comprises passages through which the gases can escape and through which air can flow when the monomer fluid is suctioned into the mixing chamber.

It can also be provided that the discharge piston is inserted in the direction of the discharge opening into the mixing chamber at least far enough that the capacity travelled over during the process is at least as large as the volume of the monomer fluid to be introduced and all connection lines via which the monomer fluid is guided into the mixing chamber.

This ensures that with the stroke of the discharge piston during pumping, a sufficient quantity of monomer fluid can be suctioned into the mixing chamber in order to produce a bone cement in the desired consistency.

With methods according to the invention, it can be provided that when the discharge piston is inserted into the mixing chamber, gas from the mixing chamber is pressed out of the device through the discharge opening and through at least one passage in a vessel for the monomer fluid. It can alternatively or additionally be provided that when the monomer fluid is suctioned into the mixing chamber, air then flows into the vessel through at least one passage in a vessel for the monomer fluid.

The vessel comprises the at least one passage so that through the at least one passage gases can escape when gas is pressed out of the mixing chamber, and air can then flow in when the monomer fluid is suctioned into the mixing chamber. This ensures that on the one hand, a good vacuum or a good underpressure can be generated in the mixing chamber, and that the monomer fluid can easily be suctioned from the vessel for the monomer fluid into the mixing chamber without an underpressure or a vacuum arising between the monomer fluid and the vessel for the monomer fluid, which counteracts the flow of the monomer fluid into the mixing chamber.

Further, it can be provided that the monomer fluid and the first component of the bone cement, in particular the monomer fluid and the bone cement powder, react with each other in the area of an opening for the monomer fluid into the mixing chamber, in particular in the area of a nozzle, wherein as a result, the opening, in particular the nozzle, is cemented.

Through the cementing of the opening or the nozzle, an entrance of mixing bone cement paste into the connection line of the monomer fluid is prevented.

Further, it can be provided that after mixing the initial components of the bone cement, the mixing rod is pulled out of the mixing chamber until the mixing device lies on the underside of the discharge piston, wherein preferably, the mixing rod is then broken off on a determined breaking point which then lies above the discharge piston or above the locking element.

Finally, it can be provided that as a last step, the cartridge is detached from the connection line and if applicable from the foot part and is inserted into an extrusion device for extruding the bone cement from the cartridge.

The invention is based on the surprising finding that with the device and method according to the invention, it is possible to use the discharge piston both for discharging the mixed bone cement and as a pump for suctioning in the monomer fluid, wherein the same mixing rod, which is also used to operate the mixing device for thoroughly mixing the content of the mixing chamber, can simultaneously be used for operating the pump or for operating the discharge piston as a pump. All this is achieved with a closed system, in which the user cannot come into contact with the bone cement powder and with a suitable structure also cannot come into contact with the monomer fluid. With a further development, the discharge piston can also be used as a powder-tight passage for sterilising the content of the mixing chamber. As a result, it is achieved that the structure of the device is kept simple and remains low-cost. Through the avoidance of more complex structures, which must withstand greater forces, such as motors, energy storage devices, feed lines or metallic threaded rods with metallic bearings, the device can entirely or at least to a very large extent be built from plastic, so that the device can be designed as a low-cost disposable product, which is advantageous due to the hygiene standards applicable to a device for producing bone cement due to its use in patient operations.

The invention is based on the idea that the cartridge which is already available can itself be used as a pump housing and the discharge piston can be used as a pump piston with the mixing rod as an actuating element in order to generate an underpressure in the cartridge. With this underpressure, the monomer fluid is suctioned into the cement powder from the opened monomer fluid vessel into the cartridge via a connection line. Surprisingly, it was found that the underpressure generated through the manual axial upwards movement of the discharge piston in the cartridge is sufficient in order to securely transfer the monomer fluid from the opened monomer vessel into the mixing chamber to the cement powder.

An exemplary device according to the invention for mixing PMMA bone cement and for storing the initial components of the PMMA bone cement can for example be compiled from
- a) a cylindrical discharge piston with a first hollow chamber (as the passage of the discharge piston) which is restricted by a gas impermeable upper side and an underside which is gas permeable and impermeable to powder particles, and a sheath surface, wherein the sheath surface has at least one gas permeable through hole, wherein an axially movable mixing rod is guided in a gas-tight manner through the upper side of the discharge piston, through the first hollow chamber and through the underside of the discharge piston,
- b) a detachable locking element on the upper side of the discharge piston for detachably affixing the mixing rod, wherein preferably, the locking element is non-detachably connected to the discharge piston,
- c) a sealing element which encircles on the sheath surface of the discharge piston, which is arranged below the gas permeable through hole,
- d) a sealing element which encircles on the sheath surface of the discharge piston, which is arranged above the gas permeable through hole,
- e) at least one latching element on the outer sheath surface of the discharge piston,
- f) a cylindrical cartridge, wherein an upper front side of the cartridge is closed with the discharge piston, and wherein the lower front side of the cartridge is closed with a closure which is impermeable to cement powder but permeable for fluids,
- g) a second hollow chamber, which is formed by the inner chamber with the discharge piston and with the cartridge limited by the closure, wherein cement is disposed in the second hollow chamber,
- h) wherein the second hollow chamber is connected to a fluid permeable connection line via a closure which is impermeable to powder and permeable for fluid,
- i) a monomer fluid vessel and an opening element,
- j) wherein the fluid permeable connection line is connected to the opening element of the monomer fluid vessel,
- k) a mixing device which is affixed in the second hollow chamber on the end of the mixing rod, and
- l) a manually operating actuating element on the end of the mixing rod outside the cartridge.

According to a further development of the present invention, it can be provided that during the gas sterilisation with ethylene oxide, the discharge piston is pressed into the cartridge sufficiently deeply that the at least one gas permeable opening in the sheath surface of the discharge piston protrudes over the upper edge of the cartridge or the first hollow cylinder, wherein the lower sealing element of the discharge piston lies in a gas-tight manner on the inner side of the cartridge, i.e. on the edge of the mixing chamber. Following sterilisation with ethylene oxide, before the monomer transfer, the discharge piston is pushed into the mixing chamber or first hollow chamber of the cartridge in such a manner that the gas impermeable upper side of the discharge piston is deeper than the outer edge of the cartridge, wherein on the inner side of the cartridge and the second hollow chamber, i.e. the mixing chamber, the upper sealing element of the discharge piston closes in a gas-tight manner on the upper side of the cartridge.

According to a further development of the present invention, it can also be essential for the function of the device that with a maximum axial displacement of the discharge piston in the cartridge in the direction of the discharge piston, a third hollow chamber is formed above the discharge piston, which is formed by the open upper side of the cartridge and the inner surface of the cartridge, wherein the volume of the third hollow chamber is the same as or larger than the total of the volumes of the monomer fluid and the connection line.

A method according to the invention for mixing a bone cement with a device according to the invention as with the device described as an example can be characterized for example by the following chronological steps:
- a) the mixing rod is locked on the discharge piston by means of the locking element,
- b) by detaching the latching mechanism, the discharge piston can be moved axially in the cartridge,
- c) via the actuation element of the mixing rod, the mixing rod is moved downwards in the direction of the cement powder with the discharge piston affixed to it, wherein the air present in the second hollow chamber exits through the closure,
- d) the downward movement of the discharge piston is continued at least so far until the volume of the third hollow chamber is at least the same as the total of the volumes of the monomer fluid and the connection line,
- e) by actuating the opening element, the monomer fluid vessel is opened,
- f) then the mixing rod with the discharge piston affixed to it is pulled upwards manually with the actuation element, wherein an underpressure arises on the underside of the discharge piston and the monomer fluid is suctioned in,
- g) the monomer fluid from the monomer fluid vessel flows through the connection line and the closure into the cartridge to the cement powder, h) the discharge piston is reversibly connected to the cartridge via the latching mechanism,
i) the locking element is detached
j) the mixing rod which can be moved axially is manually moved axially for mixing the cement powder with the monomer fluid until a homogeneous cement paste has been created,
k) the mixing rod is pulled upwards until the mixing device lies on the underside of the discharge piston, and
l) the mixing rod is broken off on the determined breaking point which is formed above the locking element of the affixed mixing rod.

A second exemplary method according to the invention is characterized by the following successive steps:
a) the mixing rod is locked on the discharge piston by means of the locking element,
b) by detaching the latching mechanism, the discharge piston can be moved axially in the cartridge,
c) by actuating the opening element, the monomer fluid vessel is opened,
d) via the actuation element of the mixing rod, the mixing rod is moved downwards in the direction of the cement powder with the discharge piston affixed to it, wherein the air present in the second hollow chamber exits through the closure into the connection line and escapes through an opening in the opening element into the surrounding atmosphere,
e) the downward movement of the discharge piston is continued at least so far until the volume of the third hollow chamber is at least the same as the total of the volumes of the monomer fluid and the connection line,
f) then the mixing rod with the discharge piston affixed to it is pulled upwards manually with the actuation element, wherein an underpressure arises on the underside of the discharge piston and the monomer fluid is suctioned in,
g) the monomer fluid flows out of the monomer fluid vessel through the connection line and the closure into the cartridge to the cement powder,
h) by means of the latching mechanism, the discharge piston is reversibly connected to the cartridge,
i) the locking element is detached,
j) the mixing rod which can be moved axially is manually moved axially for mixing the cement powder with the monomer fluid until a homogeneous cement paste has been created,
k) the mixing rod is pulled upwards until the mixing device lies on the underside of the discharge piston, and
l) the mixing rod is broken off on the predetermined breaking point which is formed above the locking element of the affixed mixing rod.

Also according to the invention is a method in which after step l) of the two methods described above, the cartridge is detached from the foot part and is connected to an extrusion device.

Further exemplary embodiments of the invention will now be explained below with reference to five schematic figures, although without restricting the invention, in which.

Figure 1:
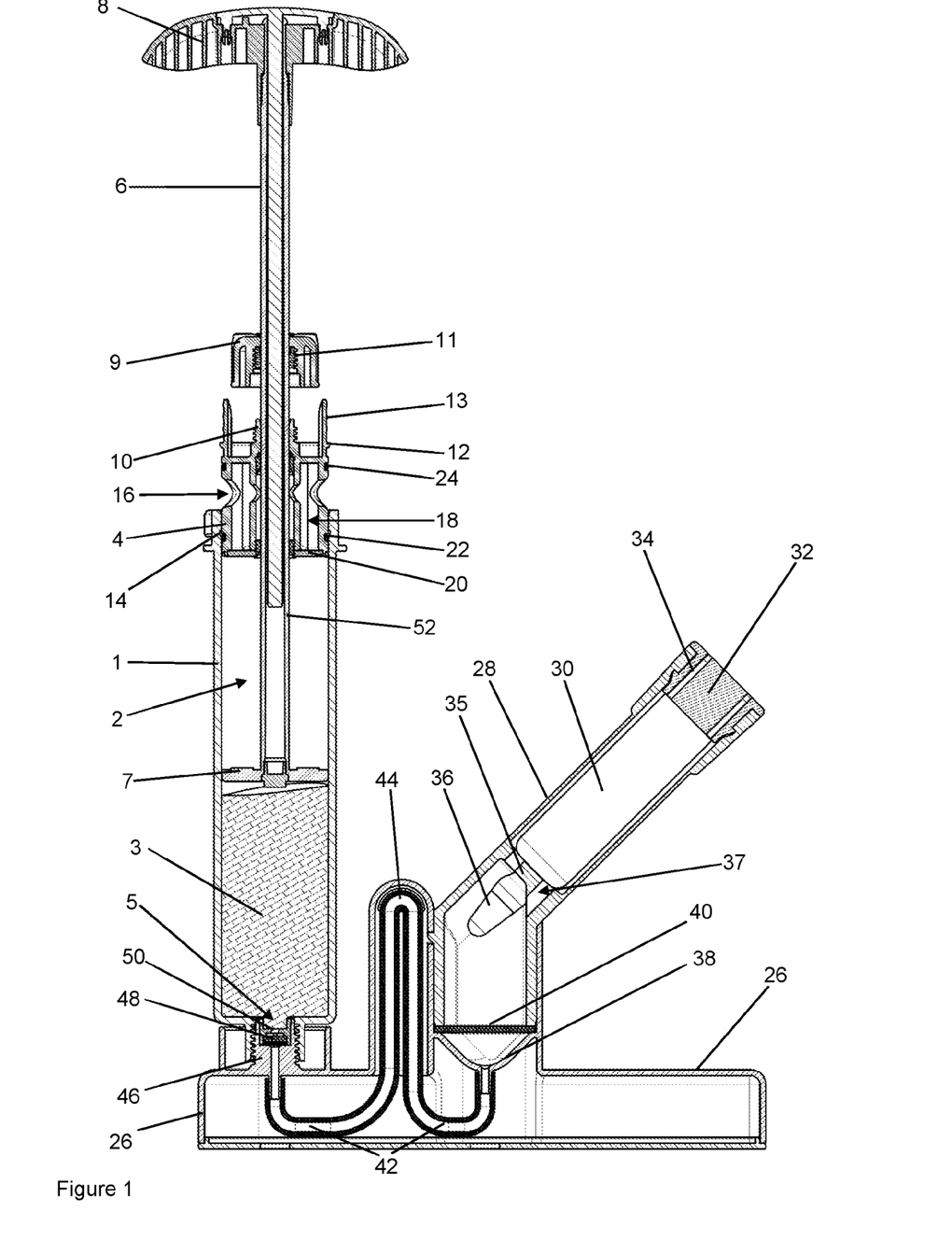
FIG. 1: shows a schematic profile view of a device according to the invention for mixing a bone cement and for storing the initial components.
Figure 2:
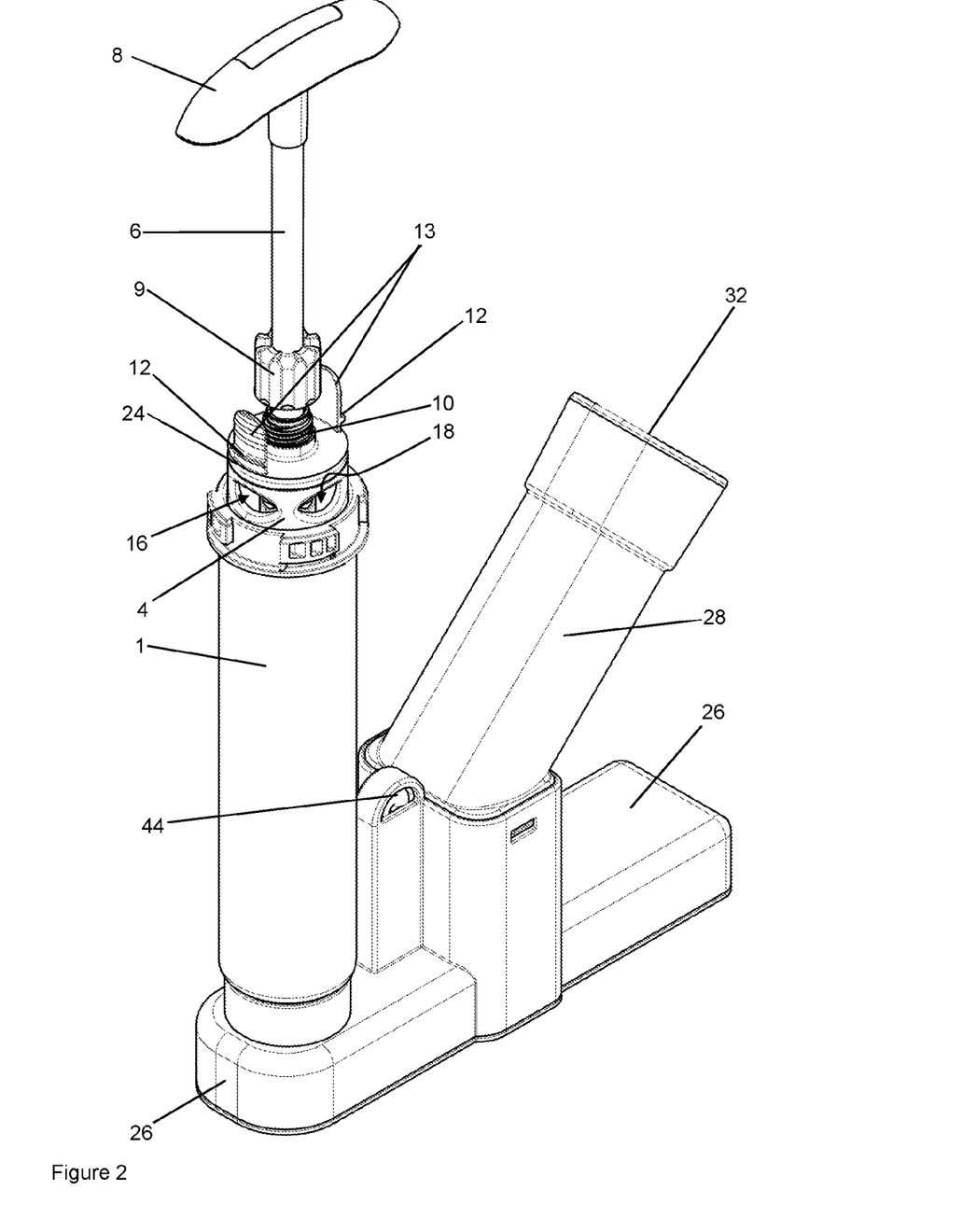
FIG. 2: shows a schematic perspective view of the device as shown in FIG. 1.
Figure 3:
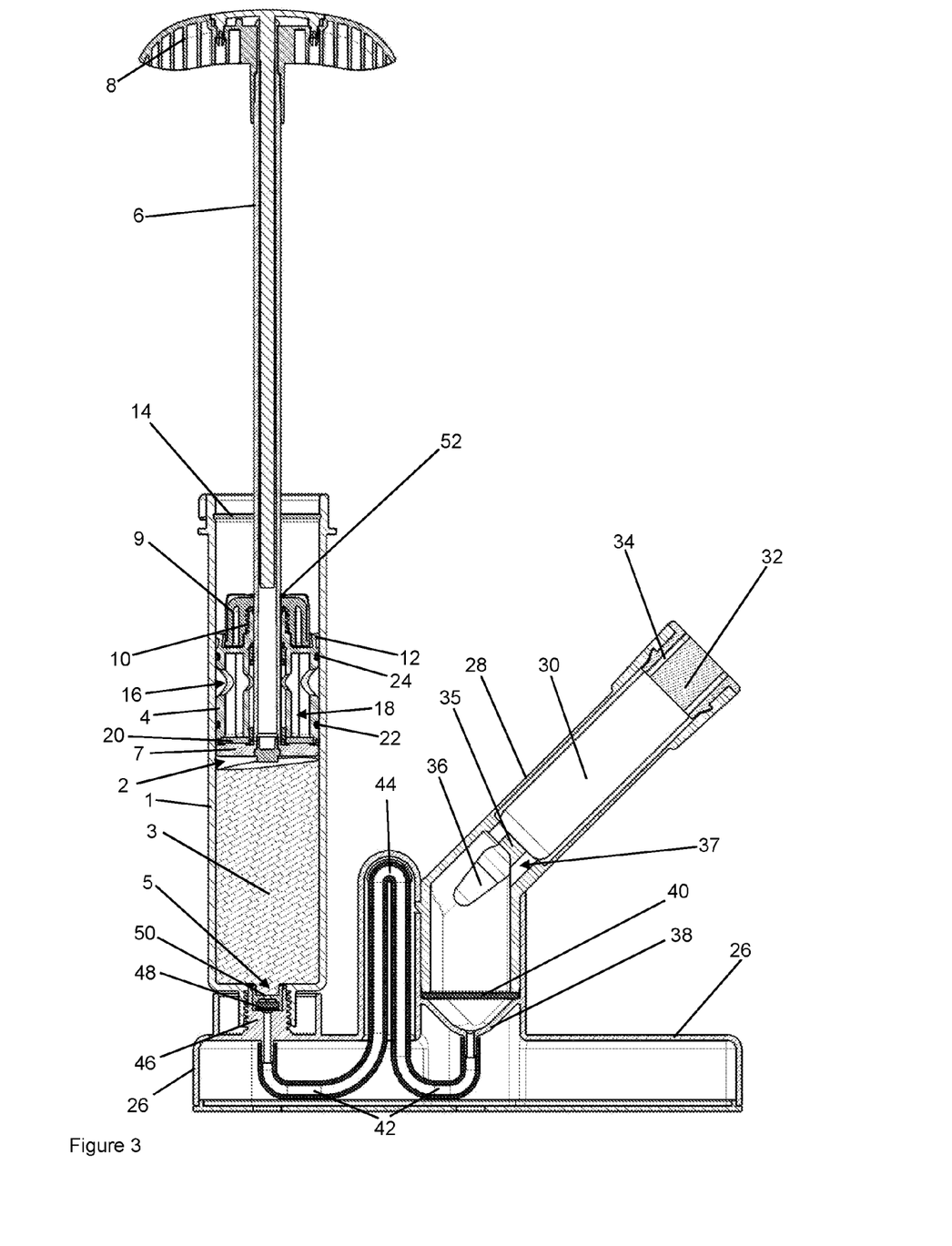
FIG. 3: shows a schematic profile view of an alternative device according to the invention without operating elements for detaching the latching mechanism prior to the pump process.
Figure 4:
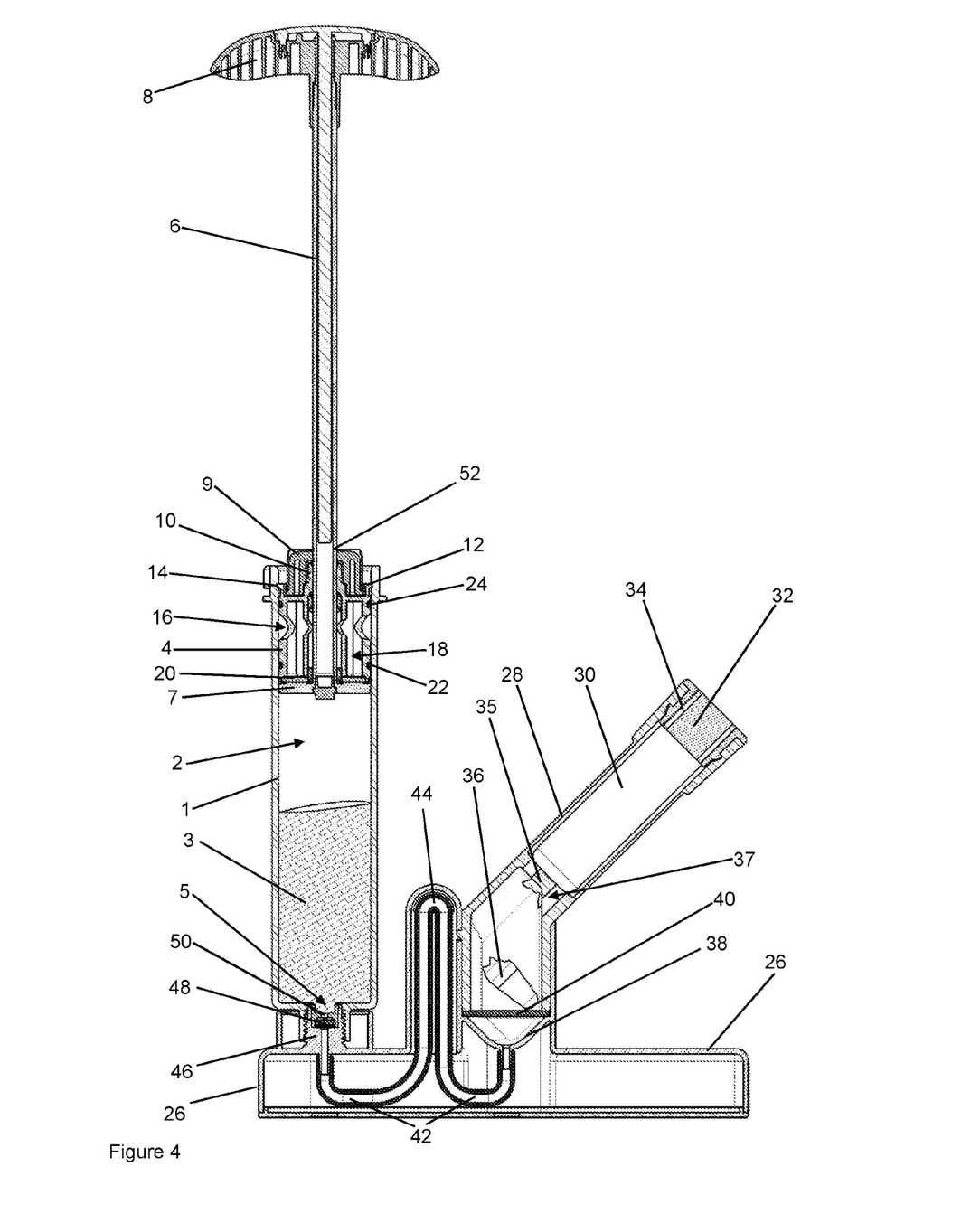
FIG. 4: shows a schematic profile view of the device as shown in FIG. 3 following the pump process.
Figure 5:
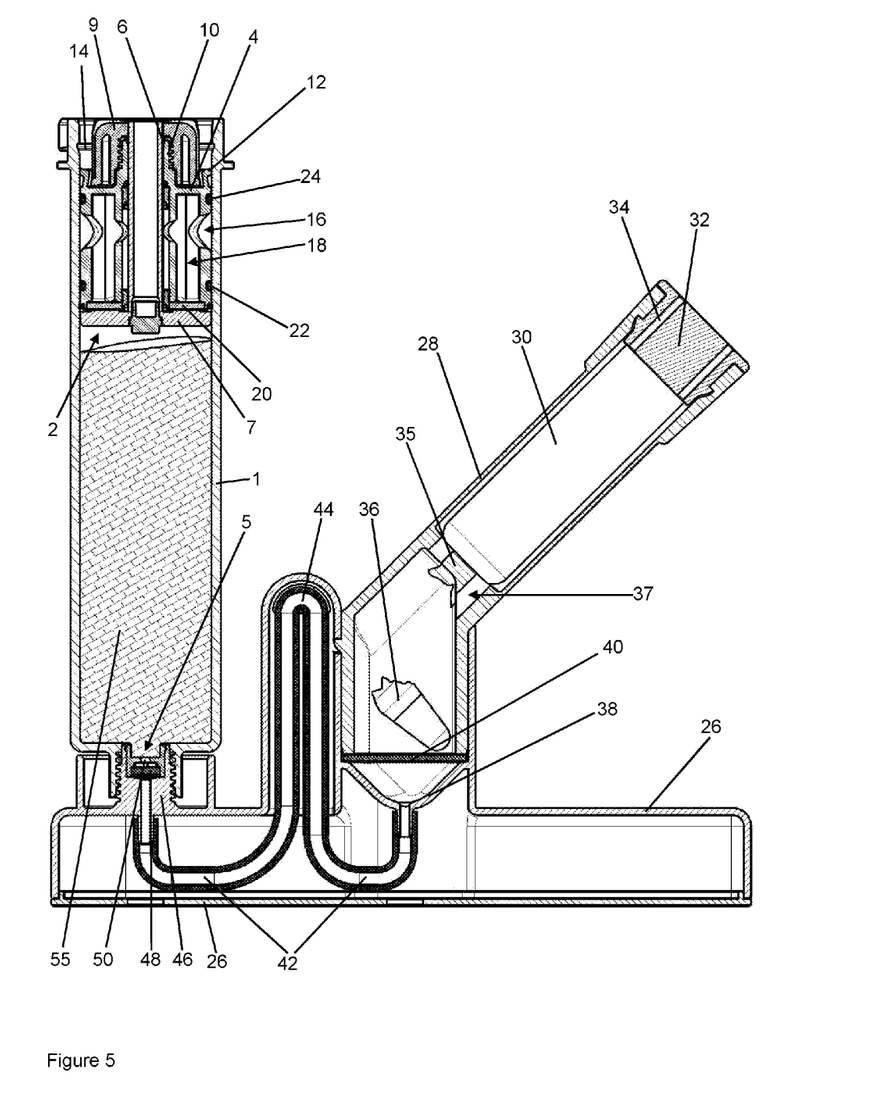
FIG. 5: shows a schematic profile view of the device as shown in FIGS. 3 and 4 following the mixing of the bone cement.

FIGS. 1 and 2 show a first method according to the invention for mixing bone cement and for storing the initial components of a bone cement in a profile view (FIG. 1) and in a perspective side view (FIG. 2). FIGS. 3 to 5 show schematic profile views of an alternative device for mixing bone cement and for storing the initial components of a bone cement, wherein these only differ from the embodiment as shown in FIGS. 1 and 2 in that the latching mechanism cannot be detached externally with the aid of operating elements 13. Due to the high degree of similarity of the exemplary embodiments, the same or similar elements in both figures are labelled with the same reference numerals, even when the elements may differ. The sequence of a method according to the invention is described with FIGS. 3 to 5. The method can however also be conducted in the same way in a convenient manner with the device as shown in FIG. 1 or 2, wherein the latching mechanism is manually detached via the operating elements 13 and not by exerting a pressure (see below). Both devices comprise a device according to the invention for mixing bone cement which must be understood as being a part of the devices for mixing bone cement and for storing the initial components of a bone cement.

The device for mixing bone cement and for storing the initial components of a bone cement in a profile view comprises a cartridge 1 in the interior of which a mixing chamber 2 is provided, which is restricted on its side by the walls of the cartridge 1. The cartridge 1 is cylindrical and the mixing chamber 2 specified by the inner walls of the cartridge 1 is also cylindrical. In the interior of the mixing chamber 2, a bone cement powder 3 is located as a first component of the PMMA bone cement to be produced. The mixing chamber is restricted on the upper side by a discharge piston 4 and on the opposite underside by an end wall with a discharge opening 5. The discharge piston 4 is formed to fit the cylindrical inner walls of the cartridge 1 and is arranged in the mixing chamber 2 or the cartridge 1 in such a manner that it can be moved in the longitudinal direction (in FIGS. 1, 3, 4 and 5 upwards and downwards).

A mixing rod 6 extends through a centric and sealed passage in the discharge piston 4. The mixing rod 6 can be moved in a linear manner in the longitudinal direction and can be turned around its own axis against the discharge piston 4 in order to move a mixing device with mixing fins 7, which is located in the mixing chamber 2. With the mixing device 7 and the mixing rod 6, the content of the mixing chamber 2 can be manually thoroughly mixed. For this purpose, a handle 8 is attached to the mixing rod 6 with which the mixing rod 6 and thus the mixing device 7 can be moved.

A screw cap 9 is arranged around the mixing rod 6, which together with a sleeve with an outer thread 10, which is attached to the discharge piston 4, or is designed as a single part with the discharge piston 4, forms a locking element 9, 10, with which the mixing rod 6 can be affixed to the discharge piston 4, wherein the screw cap 9 is screwed onto the outer thread 10. For this purpose, the screw cap 9 comprises an inner thread 11 which matches the outer thread 10. The sleeve with the outer thread 10 is slit in multiple places in the longitudinal direction and the inner thread 11 is designed to narrow in a slightly conical manner, so that the sleeve with the outer thread 10 is pressed onto the mixing rod 6 when the screw cap 9 is screwed onto the outer thread 10. As a result, a stable and detachable affixation of the mixing rod 6 to the discharge piston 4 can be achieved. Alternatively, a pin or bolt (not shown) could also be pushed through a passage (not shown) in the mixing rod 6 in order to block a movement of the mixing rod 6 into the interior of the mixing chamber 2. Further embodiments for other locking elements are certainly feasible.

On the discharge piston 4, two latching elements 12 are provided which with the embodiment as shown in FIGS. 1 and 2 can be manually detached with an operating element 13 when they are latched into place. With the embodiment as shown in FIGS. 3 to 5, the latching elements 12 are simply detached by means of sufficient pressure, which can be exerted with the affixed mixing rod 6 onto the discharge piston 4 and thus onto the latching elements 12. In order to enable the latching elements 12 to latch into place and thus affix the discharge piston against the cartridge 1, a groove 14 is provided in the inner circumference of the cartridge as a counter-latching means 14. The counter-latching means 14 is designed to have a steeper gradient in the direction of the handle 8 than in the direction of the discharge opening 5, so that the discharge piston 4 may be more deeply inserted into the mixing chamber 2, but cannot easily be pulled upwards out of the mixing chamber 2 or the cartridge 1.

The discharge piston 4 comprises in the side sheath surface several side openings 16 which lead into the interior of the discharge piston 4 and which are connected to a passage 18 which leads to the lower surface of the discharge piston 4 (which leads to the surface of the discharge piston 4 facing the discharge opening 5). As a result, the passage 18 connects the side openings 16 of the discharge piston 4 with the mixing chamber 2 and thus the mixing chamber 2 to the environment of the cartridge 1. In order to prevent bone cement powder 3 from penetrating outwards, on the lower surface of the discharge piston 4, a pore disc 20 is arranged which completely covers the passage 18 and which is impermeable to powder particles of the bone cement powder 3, while at the same time being permeable for gas. As a result, the mixing chamber 2 can be evacuated and a sterilising gas such as ethylene oxide can be fed in in order to sterilise the mixing chamber 2 and the bone cement powder 3 without the bone cement powder 3 being able to penetrate outwards. In the inner wall of the discharge piston 4, further openings are provided in the direction of the mixing rod 6 or of the passage for the mixing rod 6, through which the sterilising gas can penetrate through to the mixing rod 6 in this area. As a result, it is achieved that the device can also be sterilised in this area and thus be fully sterilised.

Between the underside of the discharge piston 4 and the side openings 16, a circumferential lower rubber seal 22 is provided with which the discharge piston 4 is sealed against the inner walls of the cartridge 1. Between the upper side of the discharge piston 4 and the side openings 16, a circumferential upper rubber seal 24 is provided with which the discharge piston 4 is sealed against the inner walls of the cartridge 1 when the discharge piston 4 is inserted sufficiently deeply into the cartridge 1. The rubber seals 22, 24 seal in a gas-tight manner. When only the lower seal 22 is inserted into the cartridge 1 (as shown in FIG. 1 and FIG. 2), gas can be introduced from the outside into the mixing chamber 2 or evacuated from the mixing chamber 2. When the upper seal 24 also lies on the inner wall of the cartridge 1, the discharge piston 4 closes the mixing chamber 2 outwardly in a gas-tight manner. The discharge piston 4 can then be used as a pump when it is moved with the mixing rod 6. For this purpose, the mixing rod 6 must be affixed to the discharge piston 4 with the aid of the locking element 9, 10.

All components described thus far, i.e. in particular the cartridge 1, the discharge piston 4, the mixing rod 6, the mixing device 7, the handle 8, the screw cap 9, the pore disc 20 and the seals 22, 24, form a device according to the invention for mixing bone cement, which is understood as being a part of a device according to the invention for mixing bone cement and for storing the initial components of the bone cement. This partial device is shown in the profile views in FIGS. 1, 3, 4 and 5 on the left-hand side (above a base foot 26). This partial device, i.e. the device for mixing bone cement, is also suitable for storing the first component of the bone cement, namely the bone cement powder 3, but is not suitable for storing the second component of the bone cement, namely a monomer fluid. The partial device can however be used individually by feeding a monomer fluid through the discharge opening 5 into the mixing chamber 2 and mixing it thoroughly with the bone cement powder 3 using the mixing device 7 in order to produce a bone cement paste.

With the present exemplary embodiments, the partial device is however combined with further components in order to form a device according to the invention for mixing bone cement and also for storing the initial components of the bone cement.

The device according to the invention for mixing bone cement and for storing the initial components of the bone cement further comprises a base foot 26 onto which the cartridge 1 is screwed and held. The base foot 26 has a flat underside and can be simply set down onto a table. Additionally, the base foot 26 holds the device together by forming a housing. An elastically deformable vessel 28 for holding a glass ampule 30 is inserted into the base foot 26. The vessel 28 consists of rubber of another elastic synthetic material. The glass ampule 30 contains a monomer fluid as a second component of the PMMA bone cement. The glass ampule 30 thus serves as a monomer fluid vessel 30 of the device. Due to the use of glass as a material, the monomer fluid can be stored for a very long time in the device, since the monomer fluid cannot easily exit through the glass.

The vessel 28 is closed with a lid 32 which is inserted as a stopper into the vessel 28. In the lid 32, several passages 34 are provided through which the air can be discharged outwards or the air can then flow into the vessel 28. The glass ampule 30 is held by the lid 32 and by a holder 35 which holds the glass ampule 30 on a neck in the area of a head 36 of the glass ampule 30. By bending the vessel 28, the head 36 can be broken off and the monomer fluid flows downwards out of the glass ampule 30. In the holder, passages 37 are provided for air exchange. When the head 36 is broken off, the glass ampule 30 (as shown in FIGS. 4 and 5), the monomer fluid flows out of the glass ampule 30 towards a funnel 38, while the head 36 and any splinters created are kept back by a strainer 40 or also a filter. The distance between the holder 35 and the strainer 40 is selected to be sufficiently large and the vessel 28 and the strainer 40 are sufficiently broad that the broken off head 36 can fall in such a manner that it can turn and come to lie on the side, so that as far as possible no or only a small quantity of monomer fluid can be held back. Instead of the elastic vessel 28 and the affixation 35 of the head 36 of the glass ampule, another opening mechanism can easily also be used with which the glass ampule 30 can be opened in the interior of the device.

When the head 36 has been broken off, the monomer fluid therefore flows through the strainer 40 and is guided by the funnel 38 into a connection line 42. The connection line 42 forms a loop 44 as a siphon, which is sufficiently high that the monomer fluid cannot flow by itself beyond the loop 44 in the direction of the cartridge 1 or the mixing chamber 2 when the monomer fluid has fully run out of the glass ampule 30. In the area of the loop 44, the housing, which is formed by the base foot 26, comprises a viewing window, through which the user can observe whether monomer fluid is guided via the loop 44 to the mixing chamber 2.

The connection line 42 opens into the mixing chamber 2 in a connecting piece 46 with an outer thread via a filter 48 which is impermeable to powder and permeable for the monomer fluid and a nozzle 50. The filter 48 prevents the bone cement powder 3 from entering the connection line 42 from the mixing chamber 2 and there reacting with the monomer fluid, hardening there and unintentionally blocking the connection line 42. With the nozzle 50, which is designed as a nozzle in accordance with U.S. Pat. No. 8,662,736 B2, it is achieved that the monomer fluid also reaches further into the interior of the bone cement powder 3 and does not become stuck in the area of the discharge opening 5, thus hindering or preventing further introduction of the monomer fluid.

The mixing rod 6 comprises a predetermined breaking point 52, which lies directly above the screw cap 9 when the screw cap is screwed onto the discharge piston 4 for attaching the mixing rod 6 to the discharge piston 4 and when the mixing rod 6 is pulled sufficiently far out of the mixing chamber 2 that the mixing device 7 lies on the underside of the discharge piston 4 as is shown in FIGS. 3 and 4.

An exemplary method will now be presented with reference to FIGS. 1 to 5. Initially, the discharge piston 4, as shown in FIGS. 1 and 2, is in a sterilisation position. The device is set into a sterilisation chamber (not shown) and air is evacuated from the sterilisation chamber. Here, the air also exits from the mixing chamber 2 through the pore disc 20 and the passage 18 of the discharge piston 4. The air is also evacuated through the passages 34 and 37 from the vessel 28 and the connection line 42, 44. Then ethylene oxide is fed in through the same openings 16, 18, 34, 37 and thus sterilises the device from the inside and the outside. The device is then removed from the sterilisation chamber.

The mixing rod 6 is then pushed sufficiently far upwards that the mixing device 7 lies on the underside of the discharge piston 4 and with the screw cap 9 the mixing rod 6 is affixed to the discharge piston 4. The discharge piston 4 is pushed with the mixing rod 6 into the cartridge 1. Here, the mixing chamber 2 closes when the upper seal 24 lies on the inner walls of the cartridge 1. The discharge piston 4 is pressed down until it reaches the bone cement powder 3. Here, the air or the gas flows out of the device from the mixing chamber 2 through the connection line 42 and the passages 37, 34. This state is shown in FIG. 3.

By bending the vessel 28, the head 36 of the glass ampule 30 is broken off and the monomer fluid flows, as described above, from the glass ampule 30 without going beyond the loop 44. Then the discharge piston 4 with the handle 8 and the mixing rod 6 is pulled upwards (away from the discharge opening 5). Here, an underpressure is created in the mixing chamber 2 with which the monomer fluid is pulled through the connection line 42, the filter 48, the nozzle 50 and the discharge opening 5 into the mixing chamber 2, where it mixes with the bone cement powder 3. The discharge piston 4 is pulled sufficiently far upwards until the latching elements 12 grip into the counter-latching means 14 and thus stops the further movement and hold the discharge piston 4 in position. This position is shown in FIG. 4.

In order to achieve a better mixing of the bone cement powder 3 with the monomer fluid, the screw cap 9 and thus the locking element 9, 10, is detached and the mixing device 7 is manually moved in the mixing chamber 2 by pushing in and pulling out the mixing rod 6 in the mixing chamber 2. If necessary, the mixing device 7 can also be turned in the mixing chamber 2. Here, the desired bone cement paste 55 is formed in the mixing chamber 2. The mixing rod 6 is again pulled out of the mixing chamber 2 until it reaches a stop, i.e. until the mixing device 7 lies on the underside of the discharge piston 4, and the mixing rod 6 is again affixed with the attachment element 9, 10 to the discharge piston 4. Then the mixing rod 6 is broken off at the predetermined breaking point 52. Now the discharge piston 4 can again be moved by detaching the latching elements 12. This arrangement is shown in FIG. 5.

Then, the cartridge 1 can be unscrewed from the base foot 26 and inserted into an extrusion device (not shown). A discharge pipe (not shown) can be screwed into the inner thread of the cartridge 1, in which a static mixer can be contained. With the extrusion device, the discharge piston 4 can then be driven forward in the direction of the discharge opening 5 and the bone cement 55 can be applied from the discharge opening 5 or the discharge pipe.

The bone cement paste 55 also already forms shortly after the start of the suctioning in process in the area of the nozzle 50 on which the monomer fluid opens out into the mixing chamber 2. When after a sufficient period of time the bone cement paste 55 has a sufficiently tough consistency, the nozzle 50 is adhered with the bone cement paste 55. This prevents the bone cement paste 55 from travelling through the nozzle 50 and into the nozzle 50 in the direction of the connection line 42. As a result, a further transfer of monomer fluid can be secured.

The larger elements of the devices of the two exemplary embodiments can essentially be produced from plastic using injection moulding.

The features of the invention disclosed in the above description and in the claims, figures and exemplary embodiments can be essential both individually and in any desired combination for the realisation of the invention in its different embodiments.

LIST OF REFERENCE NUMERALS

1 Cartridge
2 Mixing chamber
3 Bone cement powder
4 Discharge piston
5 Discharge opening
6 Mixing rod
7 Mixing fins/mixing device
8 Handle
9 Screw cap/locking element
10 Outer thread
11 Inner thread
12 Latching element
13 Operating element
14 Counter-latching means
16 Side opening
18 Passage
20 Pore disc
22 Lower seal
24 Upper seal
26 Base part
28 Container
30 Glass ampule/monomer fluid vessel 32 Lid
34 Passage
35 Holder
36 Ampule head
37 Passage
38 Funnel
40 Strainer
42 Connection line
44 Loop/siphon
46 Connecting piece with outer thread
48 Fluid permeable, powder impermeable filter
50 Nozzle
52 Predetermined breaking point
55 Bone cement paste

The invention claimed is:

1. A device for mixing a bone cement, the device comprising
   at least one cartridge comprising, in its interior, a cylindrical mixing chamber,
   a discharge piston movable, in the cylindrical mixing chamber, in the longitudinal direction and sealed against walls of the mixing chamber,
   a mixing device, for mixing the content of the mixing chamber, arranged in an interior of the mixing chamber, wherein the mixing device operable externally via a mixing rod and the mixing rod is guided through a passage in the discharge piston such that the mixing rod is rotatable and displacable in the longitudinal direction by the discharge piston,
   wherein the at least one cartridge further comprises a discharge opening opposite the discharge piston, wherein, in the mixing chamber, a first component of the bone cement is contained between the discharge piston and the discharge opening, wherein a monomer fluid as a second component of the bone cement is introducable through the discharge opening into the mixing chamber,
   wherein the device comprises a locking element with which the mixing rod is affixable or is affixed to the discharge piston such that the discharge piston is movable by means of the mixing rod in the mixing chamber in the longitudinal direction,
   and further wherein the discharge piston comprises a gas impermeable upper side that faces away from the discharge opening and a gas permeable underside, that is impermeable for powder particles, that faces towards the discharge opening, wherein the gas permeable underside is connected via at least one passage in the discharge piston with at least one side opening in the side surface of the discharge piston, such that the mixing chamber is gas-permeably connected with the environment of the cartridge, when the at least one opening in the side surface of the discharge piston is not covered by the inner wall of the mixing chamber of the cartridge.

2. The device according to claim 1, wherein the mixing rod with the locking element is detachably affixable or is detachably affixed to the discharge piston.

3. The device according to claim 1, wherein, in the discharge opening or in front of the discharge opening, a filter is provided that is impermeable for powder but permeable for fluids, which closes or covers the discharge opening.

4. The device according to claim 1, wherein at least one latching element is provided on the discharge piston, which grips into at least one counter-latching means on the cartridge such that the discharge piston can no longer be moved in the direction away from the discharge opening beyond the at least one latching position.

5. The device according to claim 4, wherein at least one of the at least one latching element is operable externally via at least one operating element.

6. The device according to claim 1, wherein the discharge piston comprises an upper circumferential seal between the gas impermeable upper side of the discharge piston and the at least one side opening and a lower circumferential seal between the gas permeable underside and the at least one side opening, which seal the discharge piston against the inner wall of the mixing chamber, or are suitable for sealing the discharge piston against the inner wall of the mixing chamber, when the discharge piston has been inserted sufficiently deeply into the cartridge in the direction of the discharge opening.

7. The device according to claim 4, wherein at least two latching positions are provided for the discharge piston, wherein the at least one side opening lies exposed in a first latching position and in a second latching position, the at least one side opening is covered.

8. The device according to claim 1, wherein, on the mixing rod, a manually operated actuation element is attached.

9. The device according to claim 1, wherein the locking element is a screw cap which encloses the mixing rod and which is screwable onto or into a counter-thread on the discharge piston such that the screw cap or the passage through the discharge piston presses onto the mixing rod such hat the mixing rod is affixed against the discharge piston, or the locking element is at least one pin which is to be inserted through at least one passage in the mixing rod, or which is to be inserted into at least one recess in the mixing rod, so that the mixing rod is no longer insertable into the mixing chamber.

10. The device according to claim 1, wherein the free volume in the mixing chamber which is not taken up by the first component and the discharge piston when the discharge piston is arranged in the cartridge at a maximum distance in the direction away from the discharge opening is at least as large as the volume of the monomer fluid to be introduced and all connection lines provided between the monomer fluid and the mixing chamber.

11. The device according to claim 1, wherein the mixing rod comprises a predetermined breaking point that is arranged directly above the upper side of the discharge piston or the locking element when the mixing rod is pulled out of the mixing chamber such that the mixing device lies on the underside of the discharge piston.

12. A cementing device, for storing the initial components of a bone cement and for mixing the bone cement, comprising the device according to claim 1 and a connection line connected to the discharge opening and which connects the mixing chamber in a fluid permeable manner with a vessel, wherein, in the vessel, a monomer vessel with a monomer fluid contained therein can be inserted or is contained, wherein the monomer vessel should be opened in the device and the monomer fluid should be suctioned into the mixing chamber through the connection line by an underpressure which is generated in the mixing chamber by a movement of the discharge piston away from the discharge opening.

13. The cementing device according to claim 12, wherein, in the vessel, at least one passage is provided, wherein the at least one passage connects the vessel with the environment in a gas permeable manner.

14. The cementing device according to claim 12, further comprising an opening device with which the monomer vessel should be opened in the vessel without hereby opening the device or without hereby opening the vessel.

15. The cementing device according to claim 12, further comprising a foot part that is connected to the cartridge and on which the vessel is also attached.

16. The device according to claim 4, wherein the at least one latching element is arranged on a side sheath surface of the discharge piston and the at least one counter-latching means is arranged on the inner wall of the mixing chamber.

17. The device according to claim 5, wherein the operating element is connected to the at least one of the at least one latching element and protrudes over the upper edge of the cartridge, wherein the upper edge of the cartridge lies opposite the discharge opening.

18. The device according to claim 17, wherein the operating element is connected as a single piece with the at least one of the at least one latching element.

19. The device according to claim 7, wherein, in the first latching position, the discharge piston is only sealed against the mixing chamber by the lower circumferential seal, and, in the second latching position, the discharge piston is sealed against the mixing chamber by the upper and lower seal.

20. The device according to claim 1, wherein the locking element is at least one pin which is to be inserted through at least one passage in the mixing rod, or which is to be inserted into at least one recess in the mixing rod, so that the mixing rod can no longer be inserted into the mixing chamber, wherein the at least one passage or the at least one recess is positioned such that the mixing device lies on the underside of the discharge piston facing towards the discharge opening, when the mixing rod is affixed against the discharge piston with the at least one pin.

21. The cementing device according to claim 12, wherein the cementing device is a full-prepacked cementing device.

22. The cementing device according to claim 15, wherein the cartridge is detachably connected to the foot part.

23. The cementing device according to claim 15, wherein the cartridge is detachably connected to the foot part via a thread.

* * * * *